United States Patent
Ohnishi et al.

(10) Patent No.: US 7,306,734 B2
(45) Date of Patent: Dec. 11, 2007

(54) METHOD FOR SEPARATION OF ENANTIOMERIC ISOMERS BY SIMULATED MOVING BED CHROMATOGRAPHY

(75) Inventors: Atsushi Ohnishi, Ibaraki (JP); Koichi Murazumi, Hyogo (JP)

(73) Assignee: Daicel Chemical Industries, Ltd., Osaka (JP)

( * ) Notice: Subject to any disclaimer, the term of this patent is extended or adjusted under 35 U.S.C. 154(b) by 321 days.

(21) Appl. No.: 10/943,436

(22) Filed: Sep. 17, 2004

(65) Prior Publication Data
US 2005/0054878 A1 Mar. 10, 2005

Related U.S. Application Data

(62) Division of application No. 10/279,738, filed on Oct. 24, 2002, now abandoned.

(30) Foreign Application Priority Data

| Apr. 12, 2002 | (JP) | ............... 2002-110542 |
| Oct. 23, 2002 | (JP) | ............... 2002-307820 |

(51) Int. Cl.
*B01D 15/08* (2006.01)

(52) U.S. Cl. .................. 210/635; 210/656; 210/659; 210/198.2; 210/502.1

(58) Field of Classification Search ............... 210/659, 210/198.2, 502.1, 635, 656
See application file for complete search history.

(56) References Cited

U.S. PATENT DOCUMENTS

| 4,786,415 A | * | 11/1988 | Shibata et al. ............... 210/635 |
| 4,818,394 A | * | 4/1989 | Okamoto et al. ......... 210/198.2 |
| 4,861,872 A | * | 8/1989 | Okamoto et al. ........... 536/18.7 |
| 5,030,354 A | * | 7/1991 | Miwa et al. ................. 210/635 |
| 5,126,055 A | * | 6/1992 | Yamashita et al. .......... 210/659 |
| 5,434,298 A | * | 7/1995 | Negawa et al. .............. 560/248 |
| 5,770,088 A | * | 6/1998 | Ikeda et al. .................. 210/659 |
| 5,772,876 A | * | 6/1998 | Murakami ............... 210/198.2 |
| 6,130,353 A | * | 10/2000 | Bopp .......................... 562/401 |
| 6,641,784 B1 | * | 11/2003 | Okamoto et al. ............. 422/70 |

FOREIGN PATENT DOCUMENTS

| JP | 07 330802 | 12/1995 |
| JP | 2001 296288 | 10/2001 |
| WO | WO 01/14288 | * 8/2000 |

OTHER PUBLICATIONS

Machine translation of Onishi (Japan Publication No. 2001-296288).*
Machine translation of Ogasawara (Japan Publication No. 07-330802).*
European Patent Office Search Report dated Jun. 28, 2005 (3 pages).

* cited by examiner

*Primary Examiner*—Ernest G. Therkorn
(74) *Attorney, Agent, or Firm*—Flynn, Thiel, Boutell & Tanis, P.C.

(57) ABSTRACT

The present invention provides a method having a high productivity for preparative separation by simulated moving bed chromatography. That is, in a filler for enantiomeric isomer separation by simulated moving bed chromatography, which has a porous carrier carrying a polysaccharide derivative thereon and has a TS coefficient in a range of 0.55 to 1.20, the TS coefficient being defined by the below-shown formula (I), and obtained by using an enantiomeric isomer separation column for simulated moving bed chromatography in which the filler is filled in a column tube by a slurry filling method:

$$TS\ coefficient = [Vc - [t(TS) - t(blank)] \times FR] / [t(TS) - t(blank)] \times FR, \quad (I)$$

wherein
$Vc$ (cm$^3$): a column volume;
$FR$ (ml/min.): a flow velocity;
$t(TS)$ (min.): an elution time for tetrakis(trimethylsilyl) silane (=TS); and
$t(blank)$ (min.): an elution time for TS in the state where the column is not connected.

19 Claims, 8 Drawing Sheets

METHOD FOR SEPARATION OF ENANTIOMERIC ISOMERS BY SIMULATED MOVING BED CHROMATOGRAPHY

This is a division of Ser. No. 10/279,738, filed Oct. 24, 2002, now abandoned.

FIELD OF THE INVENTION

The present invention relates to a filler for enantiomeric isomer separation, in particular a filler for enantiomeric isomer separation for simulated moving bed chromatography, which is suitable for preparative separation of enantiomeric isomers by simulated moving bed chromatography. The present invention also relates to a method of producing such a filler for separation, to an enantiomeric isomer separation column for simulated moving bed chromatography using such a filler for separation, and to a method of separating enantiomeric isomers by simulated moving bed chromatography using the filler.

PRIOR ART

Organic compounds have many enantiomeric isomers that have exactly the same physical and chemical properties with respect to their boiling point, melting point and solubility but have different physiological activities. Proteins composed of L-amino acids are important constituents of organisms; high-dimensional asymmetric spaces constructed by these proteins recognize organic compounds differently, which results in expression of different physiological activities. In the case of pharmaceuticals, differences in pharmacological activities due to easiness of their binding to specified receptors in an organism have been studied and cases where significant differences in efficacy or toxicity are observed between enantiomeric isomers are well known. Under the circumstances, Guideline for the Production of Pharmaceuticals issued by Ministry of Health, Labour and Welfare describes that "in the case where the drug is of a racemic form, it is desirable that absorption, distribution, metabolism, and excretion kinetics of each isomer be studied in advance".

Since as described above the physical and chemical properties of enantiomeric isomers are exactly the same, analysis cannot be performed by ordinary separation means and accordingly studies have been intensely made on a technique for easily and precisely analyzing a wide variety of enantiomeric isomers. As a result, as an analyzing technique that meets these requirements, an optical separation method by high performance liquid chromatography (HPLC), in particular an optical separation method by use of a chiral column for HPLC has been developed. The term "chiral column" as used herein refers to a column with an asymmetry recognition agent (or chiral selector) itself or with a chiral stationary phase composed of a carrier having carried thereon an asymmetry recognition agent. For example, an optically active poly(triphenylmethyl methacrylate) (JP 57-150432 A), cellulose or amylose derivative (Y. Okamoto, M. Kawashima and K. Hatada, J. Am. Chem. Soc., 106, 5337, 1984), ovomucoid, which is a protein (JP 63-307829 A), and so on have been developed.

Among these chiral stationary phases for HPLC, optical separation columns with a silica gel carrying a cellulose or amylose derivative thereon are known to have high asymmetry recognition ability for a very wide variety of compounds. Furthermore, studies on industrial-scale liquid preparative chromatography of optically active substances by using the above-mentioned chiral stationary phase for HPLC and simulated moving bed method in combination have been in progress (Pharm Tech Japan, vol. 12, 43 (1996)).

DISCLOSURE OF THE INVENTION

An object of the present invention is to provide a filler for enantiomeric isomer separation for simulated moving bed chromatography, having a high productivity suitable for preparative separation by simulated moving bed chromatography.

Another object of the present invention is to provide a method of producing a filler for such a separation.

Still another object of the present invention is to provide an enantiomeric isomer separation column for simulated moving bed chromatography using the separation filler.

Yet another object of the present invention is to provide a method of separating an enantiomeric isomer using them.

Therefore, according to the present invention, there is provided a filler for enantiomeric isomer separation for simulated moving bed chromatography having a porous carrier carrying a polysaccharide derivative thereon, characterized in that the filler has a TS coefficient in a range of 0.55 to 1.20, the TS coefficient being defined by the below-shown formula (I), and obtained by using an enantiomeric isomer separation column for simulated moving bed chromatography in which the filler is filled in a column tube by a slurry filling method:

$$TS\ \text{coefficient} = [Vc - [t(TS) - t(\text{blank})] \times FR] / [t(TS) - t(\text{blank})] \times FR \quad (I)$$

wherein abbreviations mean the following:
Vc ($cm^3$): a column volume;
FR (ml/min.): a flow velocity;
t(TS) (min.): an elution time for tetrakis(trimethylsilyl)silane (=TS); and
t(blank) (min.): an elution time for TS in the state where the column is not connected.

In the present invention, TS coefficient is a value measured under the following conditions).

<TS Coefficient Measuring Conditions>
Analyzer: HPLC apparatus;
Detector: UV detector, detection being performed at a wavelength of 210 nm;
Moving phase: n-Hexane/2-propanol=9/1 (v/v)
Temperature: 25° C.;
Flow velocity: ¼ to ⅑ of column volume Vc ($cm^3$).
Charge amount of TS: a TS solution having dissolved therein 5.0 mg/ml of TS in the moving phase is charged in 1/300 to 1/600 of the column volume.

The "TS coefficient" is a parameter that indicates separation ability of enantiomeric isomers derived by analyzing elution time of tetrakis(trimethylsilyl)silane, which is an evaluation sample having structurally important characteristics, and calculating it based on a standardized calculation formula. It indicates that a filler having a specified numerical range of this parameter (TS coefficient=0.55 to 1.20) is very useful as means for producing optically active substances, in particular, in HPLC preparative separation of enantiomeric isomers. At present, the following three reasons may be given as conceivable reasons for the usefulness of TS coefficient as an effective parameter.

(1) TS is a molecule having four bulky trimethylsilyl groups, which is relatively large in molecular size. Because of its symmetry, the configuration of the molecule is of a structure close to a sphere. When a predetermined amount of TS is charged, TS interacts with pores on the surface of a porous carrier which have a size suitable for enantiomeric isomer separation of low molecular substances, depending on its size and shape and is eluted from the packed column. This is just like TS observing the surface state of the filler based on the principle of size exclusion chromatography or the like. It is presumed that a filler having shorter elution time than a specified elution time is a filler (porous carrier carrying thereon a polysaccharide derivative) having a smooth surface and hence having a configuration unsuitable for enantiomeric isomer recognition. On the contrary, a filler having an elution time longer than a specified elution time has a surface that is too rough for performing uniform molecule recognition, suggesting that it is disadvantageous for enantiomeric isomer recognition.

(2) Since TS is a compound containing five silicon atoms, it can interact with the silane compound of silica gel that is usually in common use as a porous carrier (it is often the case that silica gel is surface-treated with a silane compound). Based on the extremely weak interaction, it is possible to estimate the ratio of abundance of the carrier silica gel to that of the polysaccharide derivative in the pore cavity of the carrier and existence of exposed silica gel sites due to deviation in abundance of the polysaccharide derivative. For example, if a filler has an elution time longer than a specified elution time, it indicates that the silicon on the silica gel and TS excessively interact with each other. It is conceivable that this indicates nonspecific adsorption by silica gel irrelevant to asymmetry recognition or non-uniform coating of polysaccharide derivative due to existence of exposed silica gel.

(3) TS has no functional group that can participate in interactions generally said to have a high energy, such as hydrogen bond interaction and dipole interaction. In particular, when a nonpolar solvent is used as a moving phase, the abundance equilibrium of TS between the stationary phase (filler) and moving phase (eluant) is considered to be biased toward the moving phase side.

Particularly, in an overloaded state (state where a high pressure is loaded) at the time of HPLC preparative separation, the abundance equilibrium of TS biased toward the moving phase side results in an unstable elution time. However, even in an overloaded state, if the abundance ratio between space volume and polysaccharide derivative volume is appropriate in the inside of pores of a porous carrier, the elution time becomes stable. Therefore, the abundance ratio can be estimated from an elution time, which becomes an important index for evaluating whether an HPLC preparative separation filler is suitable.

As stated above, TS coefficient is not only a parameter showing the separation ability for enantiomeric isomers but also a parameter that shows the carrying state of a polysaccharide derivative on the surface of the porous carrier. A method of producing a filler having the same TS coefficient cannot be achieved merely by using the same amount of polysaccharide derivative. Obtaining uniform carrying techniques by coating conditions such as control of smoothness or roughness of the surface state of the filler, a good stirring method, stirring mode, number of coatings, and amount of coating solvent, are also important requirements. The above-mentioned numerous complex interactions can be estimated from the elution time of TS, which is structurally the most suitable compound among an extremely large number of index compounds, and from a TS coefficient obtained based thereon according to a calculation formula set up for standardizing various packing columns. Fillers whose TS coefficient is in a specified range exhibit excellent performance, particularly as a filler for HPLC preparative separation.

Accordingly, in the present invention, TS coefficient has been introduced in order to make clear the relationship between the porosity and separation ability of a porous carrier. For example, measurement of TS coefficient for a part of the fillers in the same production lot enables one to confirm the separation ability of all the fillers in that production lot. This can significantly improve the accuracy of confirmation of separation ability as compared with the conventional confirmation means based on the carrying amount of polysaccharide derivative.

Further, according to the present invention, there is provided a method of producing an enantiomeric isomer separation filler for simulated moving bed chromatography described above, the method being characterized by including coating a porous carrier with a polysaccharide derivative dope a plurality of times.

By applying such a method, control of the pore volume becomes easier so that it becomes easier to control the porosity of the porous carrier. This makes it easy to produce an enantiomeric isomer separation filler having a desired TS coefficient. The number of coatings is preferably about 2 to 6 times.

Further, according to the present invention, there is provided an enantiomeric isomer separation column for simulated moving bed chromatography which uses the above-mentioned enantiomeric isomer separation filler (hereinafter referred to as an "enantiomeric isomer separation column"), and a method of separating enantiomeric isomers characterized by performing preparative separation of enantiomeric isomers by simulated moving bed chromatography by using the above-mentioned enantiomeric isomer separation filler or the above-mentioned enantiomeric isomer separation column.

DETAILED DESCRIPTION OF THE INVENTION

The polysaccharide derivative used in the present invention can be obtained by reacting a polysaccharide with a compound having a functional group reactive with a hydroxyl group of the polysaccharide.

The polysaccharide to be used in the present invention may be any polysaccharide, regardless of whether it is a synthetic polysaccharide, a natural polysaccharide or modified natural polysaccharide, so far as it is optically active. Preferably, it has a high regularity in its binding form.

Examples of the polysaccharide include $\beta$-1,4-glucan (cellulose), $\alpha$-1,4-glucan (amylose, amylopectin), $\alpha$-1,6-glucan (dextran), $\beta$-1,6-glucan (pustulan), $\beta$-1,3-glucan (for example, curdlan, schizofillan, etc.), $\alpha$-1,3-glucan, $\beta$-1,2-glucan (Crown Gall polysaccharide), $\beta$-1,4-galactan, $\beta$-1,4-mannan, $\alpha$-1,6-mannan, $\beta$-1,2-fructan (inulin), $\beta$-2,6-fructan (levan), $\beta$-1,4-xylan, $\beta$-1,3-xylan, $\beta$-1,4-chitosan, $\alpha$-1,4-N-acetylchitosan (chitin), pullulan, agarose, alginic acid, etc. as well as amylose-containing starch. Among these, cellulose, amylose, $\beta$-1,4-xylan, $\beta$-1,4-chitosan, chitin, $\beta$-1,4-mannan, inulin, curdlan, etc., from which high purity polysaccharides are readily available, are preferred, with cellulose and amylose being particularly preferred.

The number average degree of polymerization (average number of pyranose or furanose ring contained in one molecule) of these polysaccharides is preferably 5 or more, more preferably 10 or more. There is no particular upper limit in the number average degree of polymerization but it is desirably 1,000 or less in consideration of ease of handling.

The compound having a functional group reactive with a hydroxyl group may be any compound so far as it is selected from isocyanic acid derivatives, carboxylic acids, esters, acid halides, acid amide compounds, halogen compounds, aldehydes, alcohols and other compounds having leaving groups. Also, aliphatic, alicyclic, aromatic, or heteroaromatic derivatives of these compounds may be used.

Among the polysaccharide derivatives used in the present invention, particularly preferred ones include carbamate and ester derivatives of polysaccharides (cellulose and amylose) having 0.1 per glucose unit of a urethane bond or an ester bond.

The carrier to be used in the present invention includes a porous organic carrier or porous inorganic carrier, with a porous inorganic carrier being preferred.

Suitable examples of porous organic carriers include high polymers such as polystyrene, polyacrylamide, and polyacrylate. Suitable examples of porous inorganic carriers include silica, alumina, magnesia, glass, kaolin, titanium oxide, silicates, hydroxyapatite, etc.

The average particle diameter of the porous carrier is preferably 1 to 300 μm, more preferably 15 to 100 μm, still more preferably 20 to 50 μm. The average pore diameter of the porous carrier is preferably 200 to 8,000 Angstroms, more preferably 200 to 4,000 Angstroms, still more preferably 300 to 2,000 Angstroms. Note that the particle size of the porous carrier substantially becomes the particle diameter of the filler.

A particularly preferred carrier is silica gel, the particle size of which is preferably 1 to 300 μm, more preferably 15 to 100 μm, still more preferably 20 to 50 μm. The average pore size thereof is preferably 200 to 8,000 Angstroms, more preferably 200 to 4,000 Angstroms, still more preferably 300 to 2,000 Angstroms. To exclude the possible influence of remaining silanol on the surface, it is desirable that surface treatment is performed. However, there is no problem if no surface treatment is performed at all.

As the method of having a polysaccharide derivative carried on a porous carrier, a method of bringing a porous carrier into contact with a dope of a polysaccharide derivative dissolved in an organic solvent can be applied. This contacting method is not particularly limited and a method of stirring and contacting them in a stirring type mixer can be applied.

In this method, it is preferred that a method of dividing the dope into two to six portions and contacting the porous carrier with the polysaccharide derivative to have it carried thereon in small amounts in, for example, two to six times be applied since the porosity can be controlled to adjust the TS coefficient in a narrow range. When the dope is contacted per each portion in two to six times, the amount of dope in each time may be the same or different.

The method of having a polysaccharide derivative carried on a porous carrier may be a method of coating a polysaccharide derivative on a carrier and chemically bonding the carrier and the coated polysaccharide carrier, a method of chemically bonding polysaccharide derivatives on a carrier to each other, a method of chemically bonding polysaccharide derivatives with a third component, a method of irradiating light on polysaccharide derivatives on a carrier, a method of irradiating rays such as γ-rays on polysaccharide derivatives on a carrier, a method of using a reaction caused by irradiation of electromagnetic rays such as microwaves, or a method of using a radical reaction with a free-radical initiator. By forming further chemical bonds by such a method, a more firmly fixed filler can be obtained.

Examples of the enantiomeric isomer separation filler also include mixtures of the above-mentioned polysaccharide derivative-carrying filler and another kind of enantiomeric isomer separation filler or a filler other than an enantiomeric isomer separation filler, for example, silica gel surface-treated with octadecyl.

Upon calculation of the TS coefficient in the present invention, an elution time of tetrakis(trimethylsilyl)silane (hereinafter, referred to as "TS") in a state where the column is connected to a liquid chromatographic apparatus and that in a state where the column is not connected to a liquid chromatographic apparatus are measured and the TS coefficient defined by the formula (I) described above is calculated by using the obtained elution times.

The analytical apparatus used upon this measurement is an HPLC apparatus and the detector to be used is a UV detector which can confirm elution of TS and detects it at a wavelength of 210 nm.

The analytical conditions are the normal phase conditions, that is, elution is performed under moving phase conditions with a hydrophobic solvent as a main constituent. Specifically, it is a moving phase having a compositional ratio n-hexane/2-propanol=9/1 (v/v). Preferably, the analytical temperature is room temperature (25° C.) and flow velocity is ¼ to ⅕, particularly ¼.15 of column volume Vc (cm$^3$), that is, [Vc×(¼.15)] ml/min. Furthermore, as for the charge amount of TS, it is preferred that a TS solution having dissolved TS in a moving phase thereof at a concentration of 5.0 mg/ml is placed in a volume amount ⅓00 to ⅙00 time, particularly ¼15 time, as large as that of the column volume, i.e., [Vc×(¼15)] ml.

In the present invention, it is required that the TS coefficient calculated as described above be in a range of 0.55 to 1.20, and when it is in this range, good separation ability can be obtained. A preferred range of TS coefficient is 0.55 to 1.0, more preferably 0.60 to 1.0, and still more preferably 0.7 to 1.0. The TS coefficient may be in a range of above 1.0 but not larger than 1.20.

In the present invention, the carrying amount of the polysaccharide derivative can be set in a range suitable for the preparative separation of simulated moving bed chromatography. The content of polysaccharide derivative in the enantiomeric isomer separation filler is preferably 23 to 40% by mass, more preferably 25 to 35% by mass, and still more preferably 27 to 35% by mass.

For the enantiomeric isomer separation filler of the present invention, the mass (kg) of a mixture of enantiomeric isomers (racemic form) that can be treated a day may be set to preferably 0.1 to 4 kg-rac./kg-CSP/day, more preferably 0.1 to 2 kg-rac./kg-CSP/day, and still more preferably 0.2 to 1.5 kg-rac./kg-CSP/day per 1 kg of the filler.

Since the mass (kg) of racemic form that can be treated a day can be set in the above-mentioned range, the present invention can separate the racemic form less expensively than the asymmetric synthesis method or the diastereomer method.

The enantiomeric isomer separation filler of the present invention is preferably used in a preparative separation column of simulated moving bed chromatography for the purpose of obtaining from several mg to several kg of optically active substances.

This column has a ratio, L/D, of the length of a single column (L) to the column inner diameter (D) which is preferably 0.01 to 100, more preferably 0.01 to 60, and still more preferably 0.01 to 30 from the viewpoint of increasing the separation ability thereof.

Reference numerals 1 to 12: chambers containing filler (adsorption chambers), which are connected to each other;

Reference numeral 13: an eluant feed line;

Reference numeral 14: an extract drawing line;

Reference numeral 15: an enantiomeric isomer-containing liquid feed line;

Reference numeral 16: a raffinate drawing line;

Reference numeral 17: a recycling line; and

Reference numeral 18: a pump.

DESCRIPTION OF THE PREFERRED EMBODIMENTS

Adsorption separation by simulated moving bed chromatography is practiced by continuously cycling adsorption operation, concentration operation, desorption operation, and elution and recovery operations set forth below as basic operations.

(1) Adsorption Operation

A mixture of enantiomeric isomers is contacted with an enantiomeric isomer separation filler. The enantiomeric isomer that tends to be readily adsorbed (strongly adsorbing components) and other enantiomeric isomers that are difficult to be adsorbed (weakly adsorbing components) are recovered together with eluant as a raffinate flow.

(2) Concentration Operation

The enantiomeric isomer separation filler having adsorbed thereon strongly adsorbing components is contacted with a portion of the extract described later on to expel weakly adsorbing components remaining on the enantiomeric isomer separation filler, thereby concentrating the strongly adsorbing components.

(3) Desorption Operation

The enantiomeric isomer separation filler containing concentrated strongly adsorbing components is contacted with an eluant to expel the strongly adsorbing components from the enantiomeric isomer separation filler and the strongly adsorbing components together with the eluant are recovered as an extract flow.

(4) Eluant Recovery Operation

The enantiomeric isomer separation filler having adsorbed thereon substantially only an eluant is contacted with a portion of the raffinate flow and a portion of the eluant contained in the enantiomeric isomer separation filler is recovered as an eluant recovery flow.

In adsorption separation by simulated moving bed chromatography, the number of columns, i.e., those having the above-mentioned L/D ratio used upon performing the above-mentioned adsorption operation, concentration operation, desorption operation and elution recovery operation is preferably from 3 to 36 in total, more preferably from 3 to 18 and still more preferably from 3 to 12.

Figure 1:
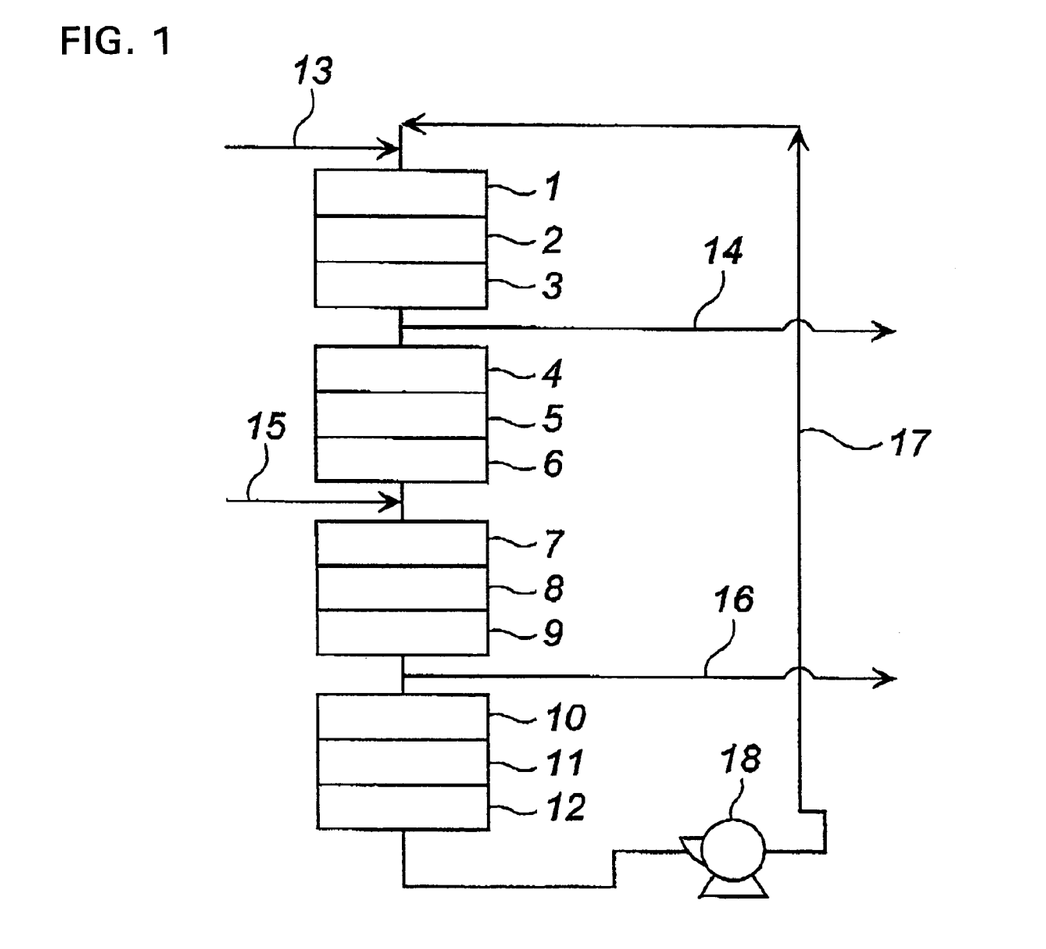
FIG. 1 is a schematic diagram illustrating one example of a simulated moving bed according to the present invention.
Figure 2:
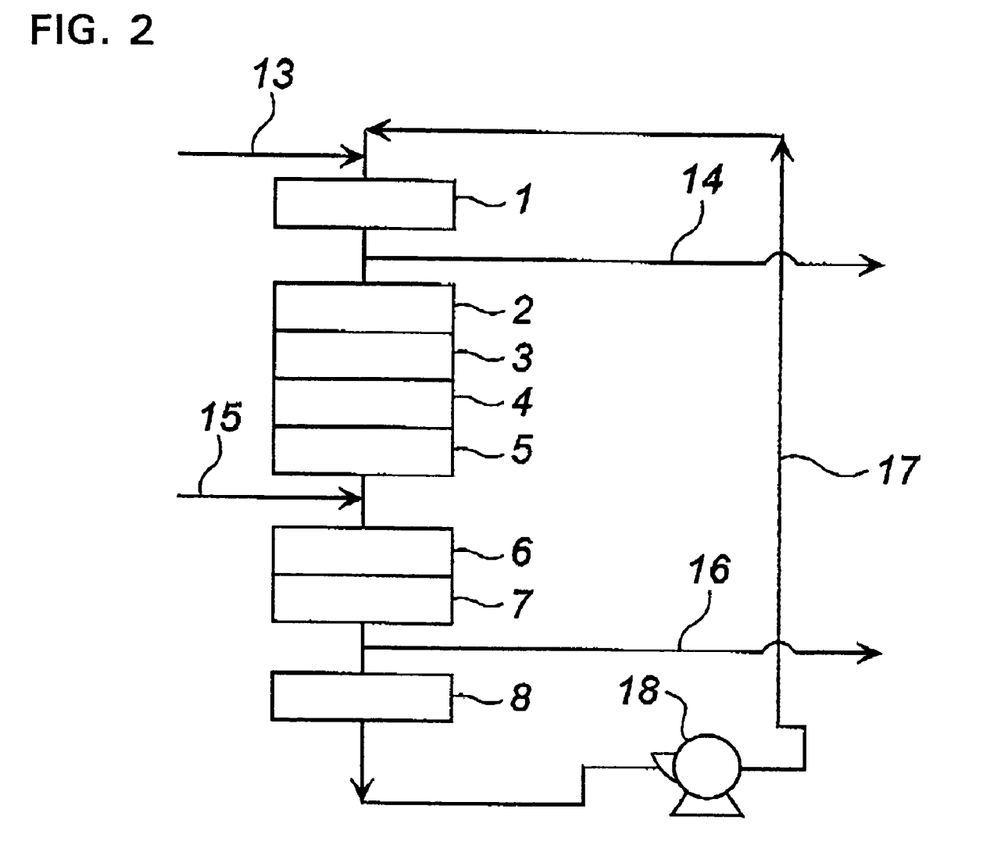
FIG. 2 is a schematic diagram illustrating another example of a simulated moving bed according to the present invention.

Hereinafter, simulated moving bed chromatography will be illustrated based on the drawings. FIG. 1 is a schematic diagram illustrating one example of a simulated moving bed according to the present invention, and FIG. 2 is a schematic diagram illustrating another example of simulated moving bed according to the present invention. In FIG. 1, the inside of a filler bed, which is a main part of the simulated moving bed, is divided into 12 unit filler beds. In FIG. 2, it is divided into eight unit filler beds. The number and size of them are determined according to the composition, flow rate, and pressure loss of the enantiomeric isomer mixture-containing solution, the size of apparatus, and the like factors and are not particularly limited.

In FIG. 1, reference numerals 1 to 12 designate chambers containing filler (adsorption chambers), which are connected to each other. Reference numeral 13 designates an eluant feed line, 14 stands for an extract drawing line, 15 indicates an enantiomeric isomer-containing liquid feed line, 16 indicates a raffinate drawing line, 17 indicates a recycling line, and 18 indicates a pump.

In the arrangement of adsorption chambers 1 to 12 and respective lines 13 to 16 shown in FIG. 1, the desorption operation is performed in the adsorption chambers 1 to 3, the concentration operation is performed in the adsorption chambers 4 to 6, the adsorption operation is performed in the adsorption chambers 7 to 9, and the eluant recovery operation is performed in the adsorption chambers 10 to 12. In such a simulated moving bed, each feed liquid and each drawing line are moved in the direction of the flow of the liquid by one adsorption chamber at a fixed time interval by valve operation. Therefore, in the next arrangement of adsorption chambers, the desorption operation is performed in the adsorption chambers 2 to 4, the concentration operation is performed in the adsorption chambers 5 to 7, the adsorption operation is performed in the adsorption chambers 8 to 10, and the eluant recovery operation is performed in the adsorption chambers 11 to 1. By repeating such operations in sequence, separation treatment of a mixture of enantiomeric isomers can be continuously and efficiently achieved.

Also, in the arrangement of adsorption chambers 1 to 8 and respective lines 13 to 16 shown in FIG. 2, desorption operation is performed in the adsorption chamber 1, the concentration operation is performed in the adsorption chambers 2 to 5, the adsorption operation is performed in the adsorption chambers 6 and 7, and the eluant recovery operation is performed in the adsorption chamber 8. In such a simulated moving bed, each feed liquid and each drawing line are moved in the direction of the flow of the liquid by one adsorption chamber at a fixed time interval by valve operation. Therefore, in the next arrangement of adsorption chambers, the desorption operation is performed in the adsorption chamber 2, the concentration operation is performed in the adsorption chambers 3 to 6, the adsorption operation is performed in the adsorption chambers 7 and 8, and the eluant recovery operation is performed in the adsorption chamber 1. By repeating such operations in sequence, separation treatment of a mixture of enantiomeric isomers can be continuously and efficiently achieved.

The enantiomeric isomer separation filler for simulated moving bed chromatography, enantiomeric isomer separation column for simulated moving bed chromatography, and method of separating enantiomeric isomers according to the present invention can be applied not only to enantiomeric isomer analyzing techniques in which a wide variety of chiral compounds are preparatively separated and optically resolving at a high productivity in the analysis of particularly drugs, foods, agricultural chemicals, perfumes, etc. but also to enantiomeric isomer separation on an industrial scale using a simulated moving bed.

The present invention can provide an enantiomeric isomer separation filler and an enantiomeric isomer separation column which have a high productivity suitable for preparative separation by simulated moving bed chromatography.

EXAMPLES

Hereinafter, the present invention will be described in detail by examples. However, the present invention should not be considered to be limited to the examples.

Example 1

Amylose tris(3,5-dimethylphenyl carbamate)-carrying Enantiomeric Isomer Separation Filler Having a TS Coefficient=0.976

(1) Synthesis of Amylose tris(3,5-dimethylphenyl carbamate)

Under a nitrogen atmosphere, 100 g of amylose and 850 g of 3,5-dimethylphenyl isocyanate were heated and stirred in 4 liters of dry pyridine at 100° C. for 60 hours and the reaction mixture was poured into 60 liters of methanol. The solids deposited were filtered and washed with methanol, and then dried under vacuum at 60° C. for 15 hours. As a result, 335 g (yield 90%) of yellowish white powdery solids were obtained.

(2) Carrying Amylose tris(3,5-dimethylphenyl carbamate) on a Silica Gel Carrier

The amylose tris(3,5-dimethylphenyl carbamate) (87.5 g) obtained in (1) described above was dissolved in an 8.5-fold amount (wt/vol), i.e., 747 ml, of ethyl acetate. In a planetary stirrer type mixer, 162.5 g of surface inactivation-treated silica gel (average particle diameter: 20 μm, average pore size: 1,300 Angstroms) were charged and uniformly coated with a ¼ portion of the polymer dope. After completion of the coating, the solvent was distilled off under heating and under reduced pressure conditions. This procedure was repeated four times to obtain the objective amylose tris(3,5-dimethylphenyl carbamate)-carrying type filler having a TS coefficient of 0.976.

(3) Preparation of a Packed Column for HPLC from the Prepared Filler

The amylose tris(3,5-dimethylphenyl carbamate)-carrying filler having a TS coefficient of 0.976 prepared in (2) described above was packed in a stainless steel made column having a length of 25 cm, an inner diameter of 0.46 cm (L/D=54.3) by a slurry packing method to prepare an enantiomeric isomer separation column.

Example 2

Amylose tris(3,5-dimethylphenyl carbamate)-carrying Enantiomeric Isomer Separation Filler Having a TS Coefficient of 0.573

(1) Synthesis of Amylose tris(3,5-dimethylphenyl carbamate)

With the same technique as that in Example 1 (1), amylose tris(3,5-dimethylphenyl carbamate) was prepared.

(2) Carrying Amylose tris(3,5-dimethylphenyl carbamate) on a Silica Gel Carrier

The amylose tris(3,5-dimethylphenyl carbamate) (2 g) obtained in (1) described above was dissolved in 20 ml of a mixed solvent composed of chloroform/DMAc=9/1 (vol/vol) (10-fold amount (wt/vol)). In a 300-ml three-necked flask, 8 g of the surface inactivation treated silica gel used in Example 1 (2) was charged, a half amount of the polymer dope was added thereto and uniformly coated thereon by using a vane-type stirring rod. After completion of the coating, the solvent was distilled off under heating and under reduced pressure conditions. This procedure was repeated to obtain the objective amylose tris(3,5-dimethylphenyl carbamate)-carrying filler having a TS coefficient of 0.573.

(3) Preparation of a Packed Column for HPLC from the Prepared Filler

The amylose tris(3,5-dimethylphenyl carbamate)-carrying filler having a TS coefficient of 0.573 prepared in (2) described above was packed in a stainless steel column having a length of 25 cm and an inner diameter of 0.46 cm by a slurry packing method to prepare an enantiomeric isomer separation column.

Example 3

Amylose tris(3,5-dimethylphenyl carbamate)-carrying Enantiomeric Isomer Separation Filler Having a TS Coefficient of 1.092

(1) Synthesis of Amylose tris(3,5-dimethylphenyl carbamate)

With the same technique as that in Example 1 (1), amylose tris(3,5-dimethylphenyl carbamate) was prepared.

(2) Carrying Amylose tris(3,5-dimethylphenyl carbamate) on a Silica Gel Carrier

The amylose tris(3,5-dimethylphenyl carbamate) (3.6 g) obtained in (1) above was dissolved in a 7.5-fold amount (wt/vol), i.e., 27.7 ml, of a mixed solvent of chloroform/DMAc=9/1 (vol/vol). In a 100-ml wide-mouthed egg-plant type flask, 5.4 g of the surface inactivation-treated silica gel used in Example 1 (2) was charged. Then, about 6.9 ml of the polymer dope was dripped to the silica gel and stirred with a spatula to uniformly coat the silica gel therewith. After completion of the coating, the solvent was air-dried at room temperature. By repeating this procedure, the objective amylose tris(3,5-dimethylphenyl carbamate)-carrying filler having a TS coefficient of 1.092 was obtained.

(3) Preparation of a Packed Column for HPLC from the Prepared Filler

The amylose tris(3,5-dimethylphenyl carbamate)-carrying filler having a TS coefficient of 1.092 prepared in (2) described above was packed in a stainless steel made column having a length of 25 cm, an inner diameter of 0.46 cm (L/D=54.3) by a slurry packing method to prepare an enantiomeric isomer separation column.

Example 4

Amylose tris(3,5-dimethylphenyl carbamate)-carrying Enantiomeric Isomer Separation Filler Having a TS Coefficient of 0.796

(1) Synthesis of Amylose tris(3,5-dimethylphenyl carbamate)

With the same technique as that in Example 1 (1), amylose tris(3,5-dimethylphenyl carbamate) was prepared.

(2) Carrying Amylose tris(3,5-dimethylphenyl carbamate) on a Silica Gel Carrier

The amylose tris(3,5-dimethylphenyl carbamate) (750 g) obtained in (1) above was dissolved in an 8.8-fold amount (wt/vol), i.e., 6.6 liters, of chloroform/DMAc=95/5 (vol/vol). In a planetary stirrer type mixer, 1.75 kg of surface inactivation treated silica gel used in Example 1 (2) was charged and uniformly coated with a ⅓ portion of the polymer dope. After completion of the coating, the solvent was distilled off under heating and under reduced pressure conditions. This procedure was repeated three times to obtain the objective amylose tris(3,5-dimethylphenyl carbamate)-carrying type filler having a TS coefficient of 0.796.

(3) Preparation of a Packed Column for HPLC from the Prepared Filler

The amylose tris(3,5-dimethylphenyl carbamate)-carrying filler having a TS coefficient of 0.796 prepared in (2) above was packed in a stainless steel column having a length of 25 cm and an inner diameter of 0.46 cm by a slurry packing method to prepare an enantiomeric isomer separation column.

Example 5

Amylose tris(3,5-dimethylphenyl carbamate)-carrying Enantiomeric Isomer Separation Filler Having a TS Coefficient of 0.645

(1) Synthesis of Amylose tris(3,5-dimethylphenyl carbamate)

With the same technique as that in Example 1 (1), amylose tris(3,5-dimethylphenyl carbamate) was prepared.

(2) Carrying Amylose tris(3,5-dimethylphenyl carbamate) on a Silica Gel Carrier

The amylose tris(3,5-dimethylphenyl carbamate) (12.5 g) obtained in (1) above was dissolved in 125 ml of ethyl acetate (10-fold amount (wt/vol)). In a 500-ml three-necked flask, 37.5 g of surface inactivation-treated silica gel was charged. Then, a half amount of the polymer dope was added and uniformly coated on the silica gel by using a vane-type stirring rod. After completion of the coating, the solvent was distilled off under heating and under reduced pressure conditions. By repeating this procedure, the objective amylose tris(3,5-dimethylphenyl carbamate)-carrying filler having a TS coefficient of 0.645 was obtained.

(3) Preparation of a Packed Column for HPLC from the Prepared Filler

The amylose tris(3,5-dimethylphenyl carbamate)-carrying filler having a TS coefficient of 0.645 prepared in (2) above was packed in a stainless steel column having a length of 25 cm and an inner diameter of 0.46 cm by a slurry packing method to prepare an enantiomeric isomer separation column.

Comparative Example 1

Amylose tris(3,5-dimethylphenyl carbamate)-carrying Enantiomeric Isomer Separation Filler Having a TS Coefficient of 0.342

(1) Synthesis of Amylose tris(3,5-dimethylphenyl carbamate)

With the same technique as that in Example 1 (1), amylose tris(3,5-dimethylphenyl carbamate) was prepared.

(2) Carrying Amylose tris(3,5-dimethylphenyl carbamate) on a Silica Gel Carrier

The amylose tris(3,5-dimethylphenyl carbamate) (2.5 g) obtained in (1) described above was dissolved in 25 ml of ethyl acetate (10-fold amount (wt/vol)). In a 300-ml three-necked flask, 22.5 g of the surface inactivation-treated silica gel used in Example 1 (2) was charged. Then, the total amount of the polymer dope was added and uniformly coated on the silica gel by using a vane-type stirring rod. After completion of the coating, the solvent was distilled off under heating and under reduced pressure conditions to obtain the objective amylose tris(3,5-dimethylphenyl carbamate)-carrying filler having a TS coefficient of 0.342.

(3) Preparation of a Packed Column for HPLC from the Prepared Filler

The amylose tris(3,5-dimethylphenyl carbamate)-carrying filler having a TS coefficient of 0.342 prepared in (2) described above was packed in a stainless steel made column having a length of 25 cm, an inner diameter of 0.46 cm by a slurry packing method to prepare an enantiomeric isomer separation column.

Comparative Example 2

Amylose tris(3,5-dimethylphenyl carbamate)-carrying Enantiomeric Isomer Separation Filler Having a TS Coefficient of 0.289

(1) Synthesis of Amylose tris(3,5-dimethylphenyl carbamate)

With the same technique as that in Example 1 (1), amylose tris(3,5-dimethylphenyl carbamate) was prepared.

(2) Carrying Amylose tris(3,5-dimethylphenyl carbamate) on a Silica Gel Carrier

The amylose tris(3,5-dimethylphenyl carbamate) (0.3 g) obtained in (1) described above was dissolved in a 6.6-fold amount (wt/vol), i.e., 2 ml, of ethyl acetate. In a 100-ml wide-mouthed egg-plant type flask, 5.7 g of the surface inactivation-treated silica gel used in Example 1 (2) was charged. Then, the total amount of the polymer dope was dripped onto the silica gel and stirred with a spatula to uniformly coat the silica gel therewith. After completion of the coating, the solvent was air-dried at room temperature to be removed. By this procedure, the objective amylose tris(3,5-dimethylphenyl carbamate)-carrying filler having a TS coefficient of 0.289 was obtained.

(3) Preparation of a Packed Column for HPLC from the Prepared Filler

The amylose tris(3,5-dimethylphenyl carbamate)-carrying filler having a TS coefficient of 0.289 prepared in (2) above was packed in a stainless steel column having a length of 25 cm and an inner diameter of 0.46 cm by a slurry packing method to prepare an enantiomeric isomer separation column.

Comparative Example 3

Amylose tris(3,5-dimethylphenyl carbamate)-carrying Enantiomeric Isomer Separation Filler Having a TS Coefficient of 0.435

(1) Synthesis of Amylose tris(3,5-dimethylphenyl carbamate)

With the same technique as that in Example 1 (1), amylose tris(3,5-dimethylphenyl carbamate) was prepared.

(2) Carrying Amylose tris(3,5-dimethylphenyl carbamate) on a Silica Gel Carrier

The amylose tris(3,5-dimethylphenyl carbamate) (1.65 g) obtained in (1) described above was dissolved in an 8.0-fold amount (wt/vol), i.e., 13.2 ml, of ethyl acetate. In a 200-ml wide-mouthed egg-plant type flask, 9.35 g of the surface inactivation-treated silica gel used in Example 1 (2) was charged. Then, a half amount of the polymer dope was dripped onto the silica gel and stirred with a spatula to uniformly coat the silica gel therewith. After completion of the coating, the solvent was distilled off in a hot water bath under reduced conditions by use of an aspirator while rotating the flask by an evaporator. By repeating this procedure, the objective amylose tris(3,5-dimethylphenyl carbamate)-carrying filler having a TS coefficient of 0.435 was obtained.

(3) Preparation of a Packed Column for HPLC from the Prepared Filler

The amylose tris(3,5-dimethylphenyl carbamate)-carrying filler having a TS coefficient of 0.435 prepared in (2) above was packed in a stainless steel column having a length of 25 cm and an inner diameter of 0.46 cm by a slurry packing method to prepare an enantiomeric isomer separation column.

Comparative Example 4

Enantiomeric isomer separation filler (CHIRALPAKAD, trade name for a product by Daicel Chemical Industries, Ltd.) as a filler was packed in a stainless steel column having a length of 25 cm and an inner diameter of 0.46 cm by a slurry packing method to prepare an enantiomeric isomer separation column. Upon measurement, the obtained filler had a TS coefficient of 0.501.

Application Example 1

By using enantiomeric isomer separation columns for HPLC packed with fillers of silica gel carrying thereon amylose tris(3,5-dimethylphenyl carbamate) preparations prepared in Examples 1 to 5 and Comparative Examples 1 to 4, respectively, liquid chromatography was performed under the following conditions to measure the elution time of TS (tetrakis(trimethylsilyl)silane) [t(TS) (min.)] and TS coefficients were calculated therefrom according to the following formula. The measured TS elution time and calculated TS coefficients are shown in Table 1. Note that the elution time of TS in a state where no column was connected was 0.16 minutes.

<Analytical Conditions Upon TS Measurement>

Moving phase: n-hexane/2-propanol=9/1 (v/v)

Flow velocity: 1.0 ml/min.

Temperature: 25° C.

Detection: 210 nm

Charged TS concentration: 5.0 mg/ml (moving phase)

<TS Calculation Formula>

Vc: $0.23 \times 0.23 \times 3.14 \times 25 = 4.15$ cm$^3$, FR: 1.0 ml/min., t(blank): 0.16 min.

TS coefficient=$[4.15-[t(TS)-0.16] \times 1.0]/[t(TS)-0.16] \times 1.0$

TABLE 1

| Separation column | | Content of polysaccharide derivative (mass %) | Number of coating times of dope | TS elution time (min) | TS coefficient |
|---|---|---|---|---|---|
| Ex. | 1 | 35 | 4 | 2.21 | 0.976 |
|  | 2 | 20 | 2 | 2.72 | 0.573 |
|  | 3 | 40 | 4 | 2.10 | 1.092 |
|  | 4 | 30 | 3 | 2.41 | 0.796 |
|  | 5 | 25 | 2 | 2.61 | 0.645 |
| Com. Ex. | 1 | 10 | 1 | 3.15 | 0.342 |
|  | 2 | 5 | 1 | 3.27 | 0.289 |
|  | 3 | 15 | 1 | 2.96 | 0.435 |
|  | 4 | — | — | 2.84 | 0.501 |

Application Example 2

50 μl of a solution in which 50 mg of compound I of the formula below is dissolved in 1.0 ml of moving phase (ethanol) was charged in the enantiomeric isomer separation columns prepared in Examples 1 to 5 and Comparative Examples 1 to 4 to obtain chromatograms shown in FIGS. 3 to 11, respectively.

Compound I

Figure 12:
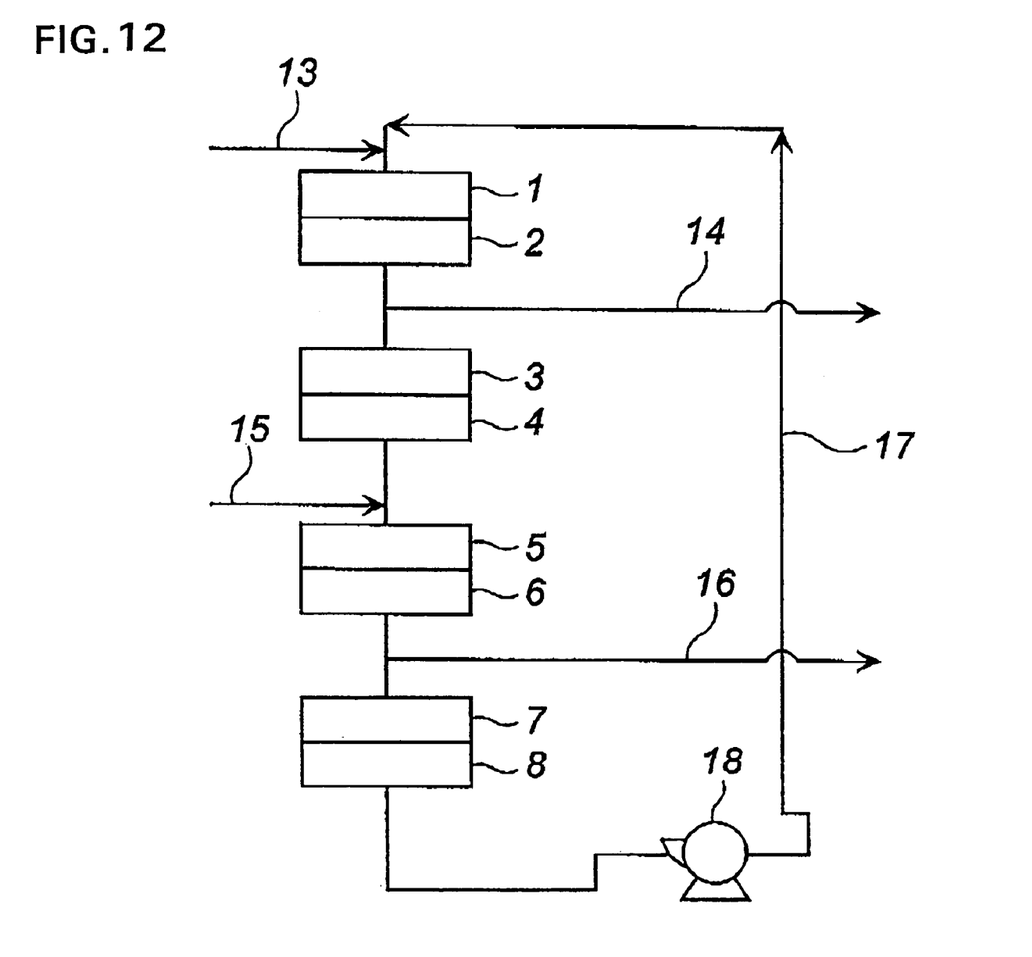
FIG. 12 is a sketch of a continuous liquid preparative chromatography apparatus of a small-sized simulated moving bed type used in Application Example 2.

Furthermore, the fillers prepared in Examples 1 to 5 and Comparative Examples 1 to 4 were packed in adsorption chambers 1 to 8 of a small-sized simulated moving bed type continuous liquid preparative chromatography apparatus shown in FIG. 12, compound I of the formula above was actually separated therein under the conditions set forth below and then raffinate component productivity of each filler was determined. The results obtained are shown in Table 2. The optical purity of the obtained raffinate components were all 97% ee or more.

<Preparative Separation Conditions>
Temperature: 25° C.
Moving phase: Ethanol
Step time: 1.5 min.
Feed concentration (concentration of compound (I)-containing ethanol solution): 50 mg/ml
Detection wavelength: 270 nm
Note that each flow velocity shown in Table 2 has the following meaning.
Feed flow velocity: Flow velocity of compound (I)-containing ethanol from line 15.
Flow velocity of raffinate: Flow velocity in line 16.
Flow velocity of extract: Flow velocity in line 14.
Flow velocity of eluant: Flow velocity of ethanol from line 13.

TABLE 2

Figure 3:
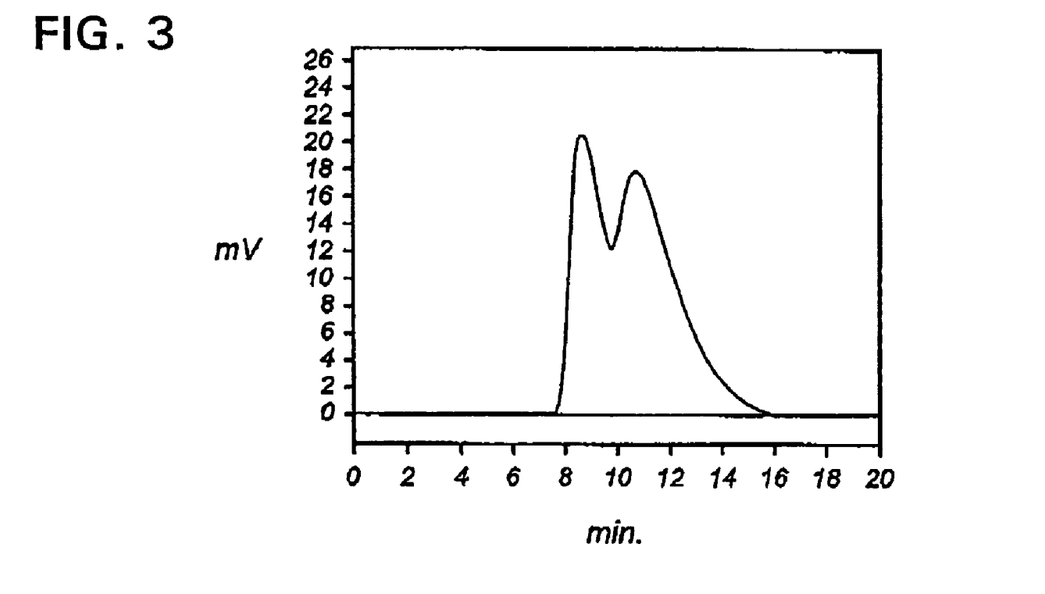
FIG. 3 is a chromatogram obtained in Application Example 2, by using the column of Example 1.
Figure 4:
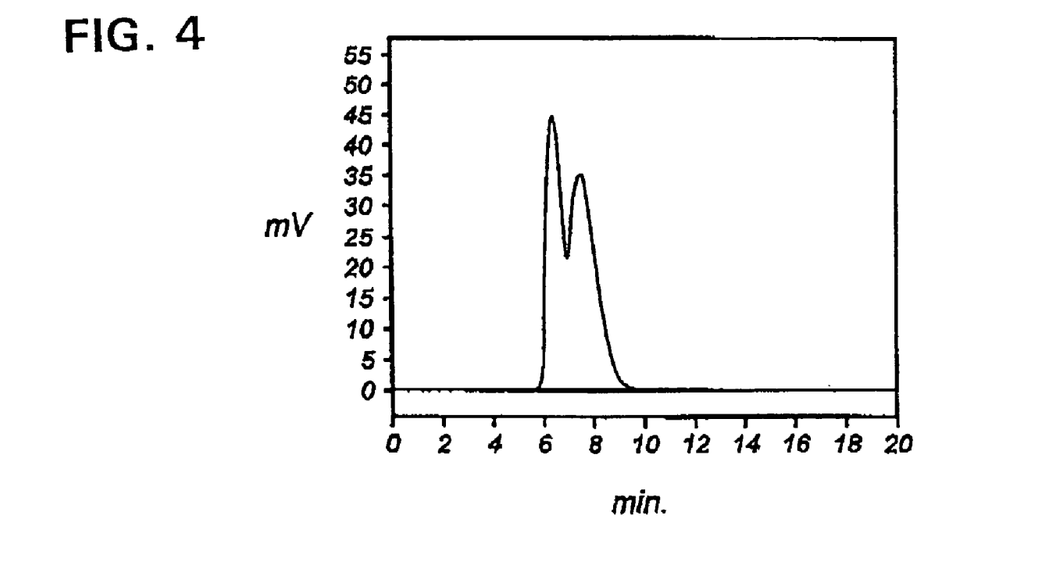
FIG. 4 is a chromatogram obtained in Application Example 2, by using the column of Example 2.
Figure 5:
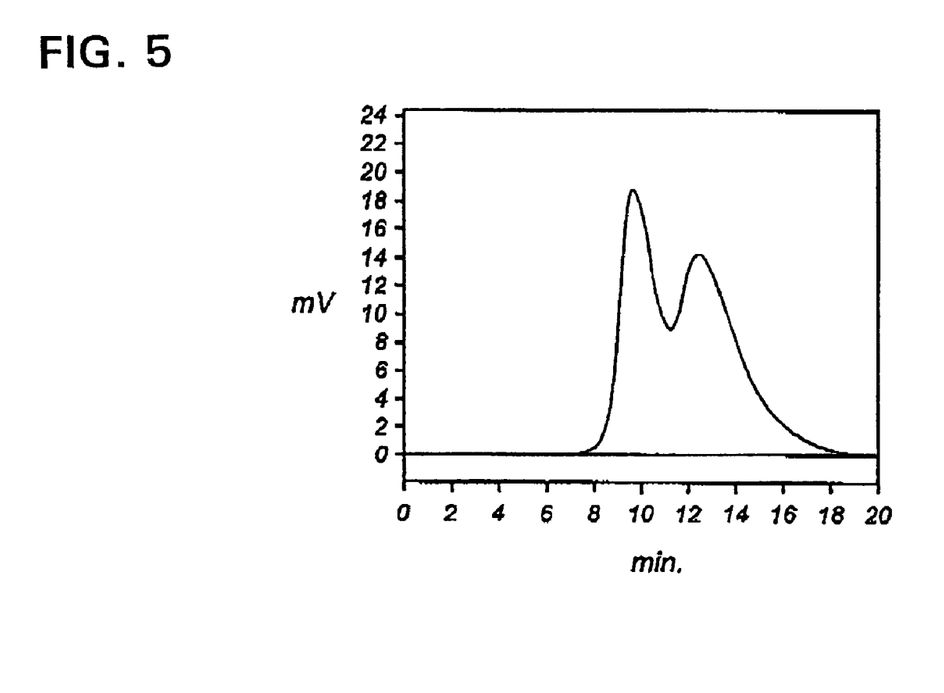
FIG. 5 is a chromatogram obtained in Application Example 2, by using the column of Example 3.
Figure 6:
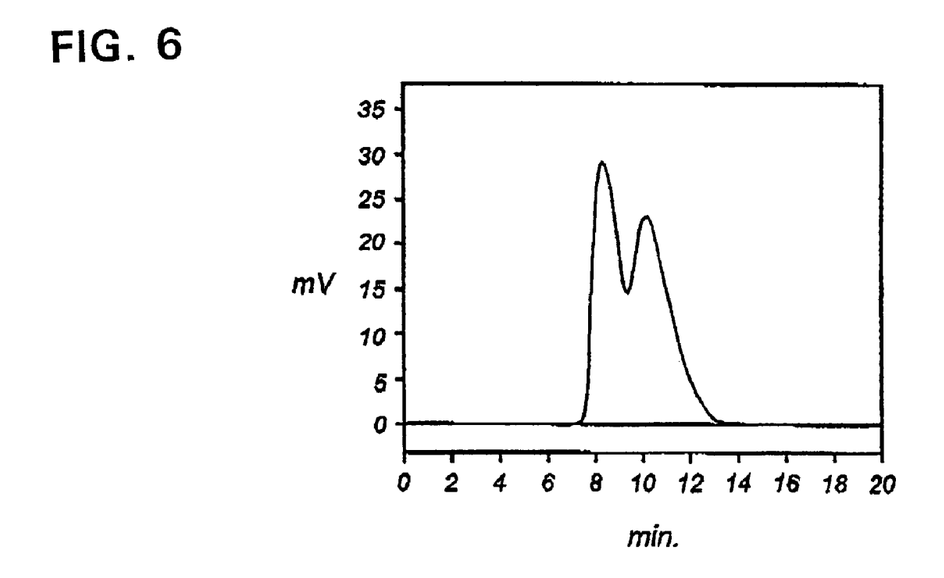
FIG. 6 is a chromatogram obtained in Application Example 2, by using the column of Example 4.
Figure 7:
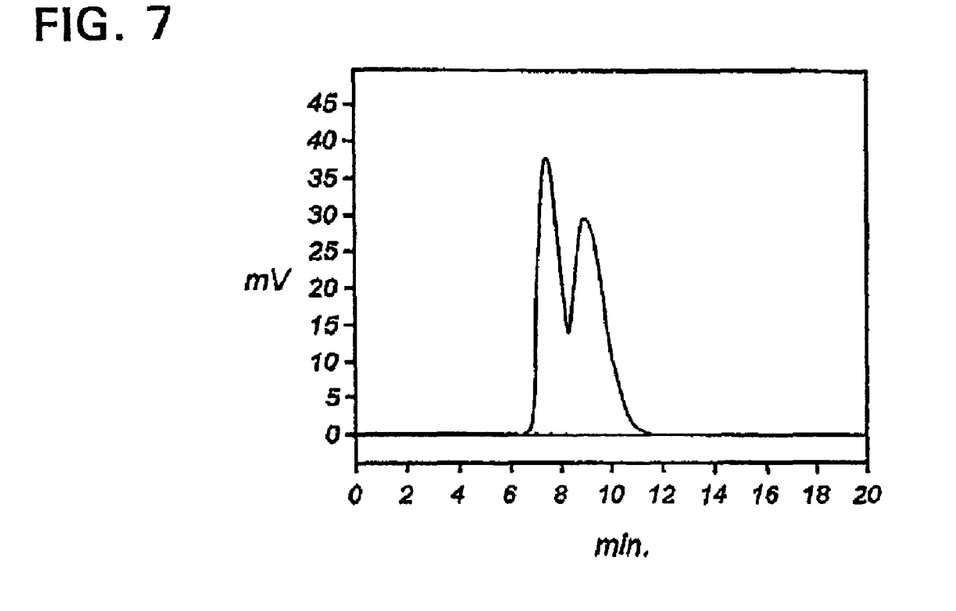
FIG. 7 is a chromatogram obtained in Application Example 2, by using the column of Example 5.
Figure 8:
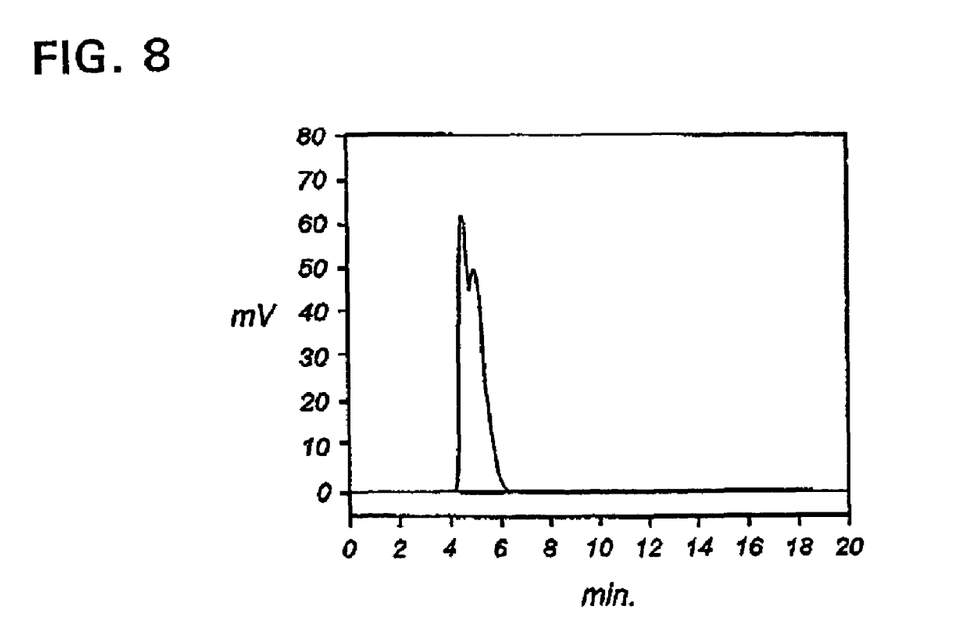
FIG. 8 is a chromatogram obtained in Application Example 2, by using the column of Comparative Example 1.
Figure 9:
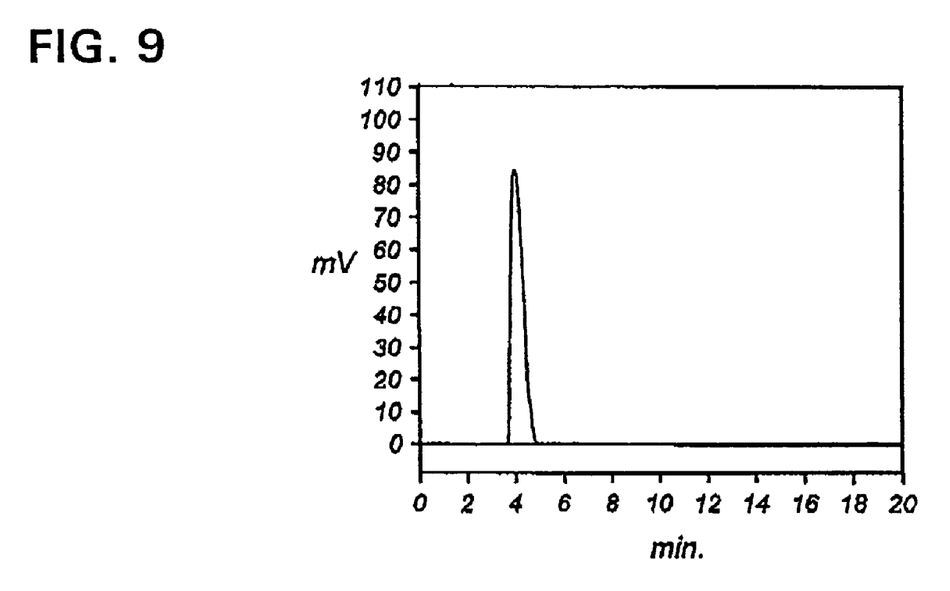
FIG. 9 is a chromatogram obtained in Application Example 2, by using the column of Comparative Example 2.
Figure 10:
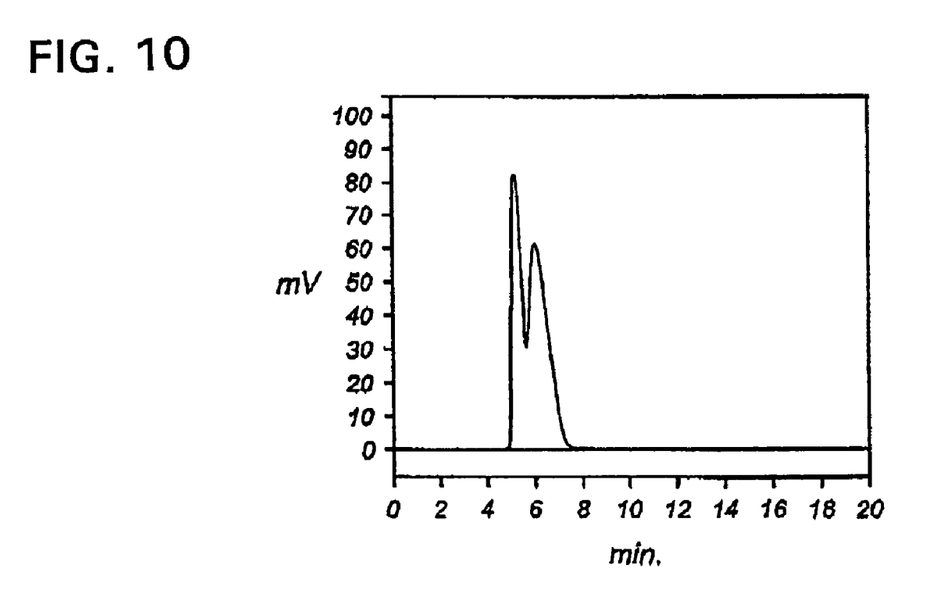
FIG. 10 is a chromatogram obtained in Application Example 2, by using the column of Comparative Example 3.
Figure 11:
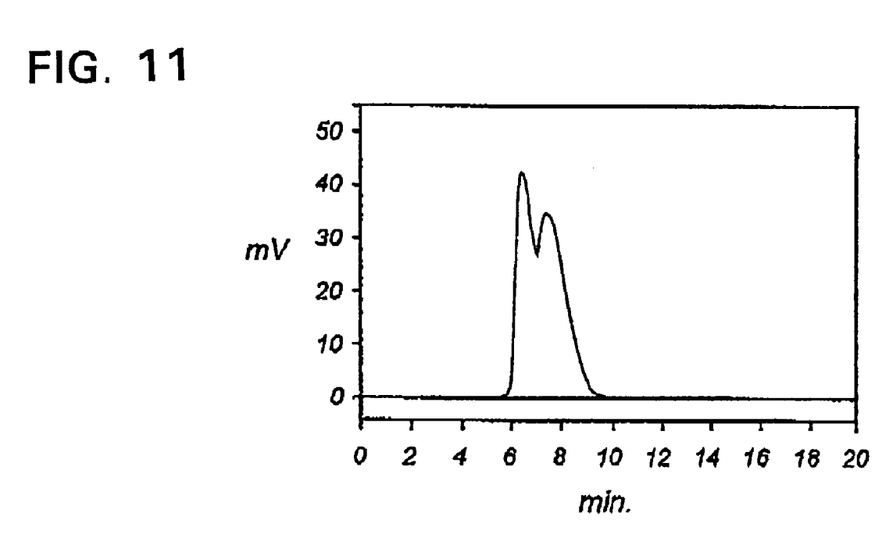
FIG. 11 is a chromatogram obtained in Application Example 2, by using the column of Comparative Example 4.

| Filler | | Content of polysaccharide derivative (mass %) | TS coefficient | Chromatogram (FIG.) | Feed flow velocity (ml/min) | Flow velocity of raffinate (ml/min) | Flow velocity of extract (ml/min) | Flow velocity of eluant (ml/mm) | Productivity*[1] |
|---|---|---|---|---|---|---|---|---|---|
| Ex. | 1 | 35 | 0.976 | FIG. 3 | 0.90 | 5.33 | 15.31 | 19.74 | 1.73 |
|  | 2 | 20 | 0.573 | FIG. 4 | 0.79 | 3.43 | 6.73 | 9.37 | 1.51 |
|  | 3 | 40 | 1.092 | FIG. 5 | 0.66 | 7.46 | 18.19 | 24.99 | 1.25 |
|  | 4 | 30 | 0.796 | FIG. 6 | 0.99 | 4.77 | 10.14 | 13.92 | 1.89 |
|  | 5 | 25 | 0.645 | FIG. 7 | 1.13 | 4.28 | 8.99 | 12.14 | 2.15 |
| Com. Ex. | 1 | 10 | 0.342 | FIG. 8 | Impossible to preparatively separate | | | | |
|  | 2 | 5 | 0.289 | FIG. 9 | Impossible to preparatively separate | | | | |
|  | 3 | 15 | 0.435 | FIG. 10 | 0.56 | 2.68 | 4.67 | 6.79 | 1.07 |
|  | 4 | — | 0.501 | FIG. 11 | 0.44 | 3.54 | 6.15 | 9.25 | 0.84 |

*[1]kg-rac./kg-CSP/day

What is claimed is:

1. In a method of separating enantiomeric isomers by simulated moving bed chromatography, the improvement comprising bringing the enantiomeric isomers into contact with a filler comprising a porous carrier carrying a polysaccharide derivative thereon in an amount of 25 to 30% by mass, the filler having a TS coefficient in a range of 0.645 to 0.796, the TS coefficient being determined by formula (I) and obtained by using an enantiomeric isomer separation column for simulated moving bed chromatography in which the filler is fitted in a column tube by a slurry filling method:

$$TS\ coefficient = [V_c - [t(TS) - t(blank)] \times FR]/[t(TS) - t(blank)] \times FR \quad (I)$$

wherein:
TS is tetrakis (trimethylsilyl) silane;
Vc (cm$^3$) is a column volume;
FR (ml/min.) is a flow velocity;
t(TS) (min.) is an elution time for tetrakis (trimethylsilyl) silane; and
t(blank) (min.) is an elution time for TS in the state where the column is not connected,
wherein the productivity is from 1.89 to 2.15 kg-rac./kg-CSP/day.

2. The method of claim 1, wherein the porous carrier is silica gel having a particle diameter of 1-300 μm and an average pore diameter of 200-8,000 Angstroms.

3. The method of claim 1, wherein the polysaccharide derivative is selected from the group consisting of a cellulose ester derivative, a cellulose carbamate derivative, an amylose ester derivative and an amylose carbamate derivative.

4. The method of claim 1, wherein the polysaccharide derivative is carried on the porous carrier in an amount of from 25 to 30% by mass.

5. The method of claim 1, wherein 0.1-4 kg of enantiomeric isomers per kg of filler are separated per day.

6. The method of claim 1, additionally comprising the step of depositing 2-6 coatings of the polysaccharide derivative onto the porous carrier.

7. The method of claim 1, wherein the polysaccharide derivative is amylose tris(3,5-dimethylphenyl carbamate).

8. The method of claim 1, wherein the simulated moving bed chromatography is performed in a column having the filler packed therein.

9. The method of claim 8, wherein the column has a ratio of column length (L) to column inner diameter (D), L/D, of 0.01 to 100.

10. The method of claim 9, wherein the column has an L/D of 0.01 to 30.

11. The method of claim 1, wherein the polysaccharide derivative is selected from the group consisting of a cellulose carbamate derivative, a cellulose ester derivative, an amylose carbamate derivative and an amylose ester derivative.

12. The method of claim 1, wherein the polysaccharide derivative is carried on the porous carrier in an amount of from 27 to 30% by mass.

13. In a method of separating enantiomeric isomers by simulated moving bed chromatography, the improvement comprising bringing the enantiomeric isomers into contact with a silica gel porous carrier having a particle diameter of 1-300 μm and an average pore diameter of 200-8,000 Angstroms and carrying thereon, in an amount of 25-30% by mass, a polysaccharide derivative selected from the group consisting of a cellulose carbamate derivative, a cellulose ester derivative, an amylose carbamate derivative and an amylose ester derivative, in an amount of from 25 to 30% by mass, the filler having a TS coefficient in the range of 0.645 to 0.796, the TS coefficient being determined by formula (I) and obtained by using an enantiomeric isomer separation column for simulated moving bed chromatography in which the filler is fitted in a column tube by a slurry filling method:

$$TS\ coefficient = [V_c - [t(TS) - t(blank)] \times FR]/[t(TS) - t(blank)] \times FR \quad (I)$$

wherein:
TS is tetrakis (trimethylsilyl) silane;
Vc ($cm^3$) is a column volume;
FR (ml/min) is a flow velocity;
t(TS) (min) is an elution time for tetrakis (trimethylsilyl) silane; and
t(blank) (min) is an elution time for TS in the state where the column is not connected, wherein the productivity is from 1.89 to 2.15 kg-rac./kg-CSP/day.

14. The method of claim 13, wherein the polysaccharide derivative is an amylose carbamate derivative.

15. The method of claim 14, wherein the amylose carbamate derivative is amylose tris(3,5-dimethylphenyl carbamate).

16. The method of claim 1, wherein the polysaccharide derivative is carried on the porous carrier in an amount of 25% by mass.

17. The method of claim 13, wherein the polysaccharide derivative is carried on the porous carrier in an amount of 25% by mass.

18. The method of claim 1, wherein the polysaccharide derivative is carried on the porous carrier in an amount of 30% by mass.

19. The method of claim 13, wherein the polysaccharide derivative is carried on the porous carrier in an amount of 30% by mass.

* * * * *